United States Patent [19]

Paparatto et al.

[11] Patent Number: 4,788,353
[45] Date of Patent: Nov. 29, 1988

[54] METHOD FOR THE SYNTHESIS OF IODOBENZENE

[75] Inventors: Giuseppe Paparatto, Milan; Marco Saetti, Priolo, both of Italy

[73] Assignee: Montedipe S.p.A., Milan, Italy

[21] Appl. No.: 22,599

[22] Filed: Mar. 4, 1987

Related U.S. Application Data

[63] Continuation of Ser. No. 784,571, Oct. 4, 1985, abandoned.

[30] Foreign Application Priority Data

Oct. 5, 1984 [IT] Italy ................................ 23004 A/84

[51] Int. Cl.$^4$ ............................................. C07C 17/15
[52] U.S. Cl. .................................... 570/203; 570/206; 570/208
[58] Field of Search ........................ 570/206, 208, 203

[56] References Cited

U.S. PATENT DOCUMENTS

| | | | |
|---|---|---|---|
| 3,363,010 | 1/1968 | Schwarzenbek | 570/203 |
| 3,600,331 | 8/1971 | Ingwalson | 570/203 |
| 3,644,542 | 2/1972 | Prahl et al. | 570/203 |
| 4,240,987 | 12/1980 | Martin et al. | 570/208 |
| 4,391,785 | 7/1983 | Rosinki et al. | 502/77 |
| 4,513,092 | 4/1985 | Chu et al. | 502/77 |

FOREIGN PATENT DOCUMENTS

| | | | |
|---|---|---|---|
| 0181790 | 5/1986 | European Pat. Off. | 570/206 |
| 77631 | 5/1982 | Japan | 570/206 |
| 159496 | 12/1963 | U.S.S.R. | 570/206 |

OTHER PUBLICATIONS

Groggins, "Unit Processes in Organic Chemistry", Fifth Ed. McGraw-Hill Book Co. Inc., (1958), p. 262.

*Primary Examiner*—Werren B. Lone
*Attorney, Agent, or Firm*—Stevens, Davis, Miller & Mosher

[57] ABSTRACT

A method for the synthesis of iodobenzene by oxydative iodination in a gaseous phase of benzene with iodine and oxygen, air or another gas containing oxygen, in the presence of a zeolitic catalyst, selected from the group comprising the zeolites of ZSM 5 and ZSM 11 type.

7 Claims, No Drawings

METHOD FOR THE SYNTHESIS OF IODOBENZENE

This application is a continuation of application Ser. No. 784,571, filed Oct. 4, 1985, now abandoned.

BACKGROUND OF THE INVENTION

The synthesis of iodobenzene starting from benzene and iodine is usually carried out in the liquid phase, in the presence of an oxidative agent; preferably the oxidative action is carried out by nitric acid (see Japanese Pat. No. 58/77830, U.S.S.R. Pat. No. 453392 and the article of Datta R. L. and Chatterjee N. R.: J. Am. Chem. Soc. 39, 437, 1917). Other oxidative agents may be used as well; none of them, however, has proved, hitherto, to be more efficient and convenient. For instance, iodic acid, sulfur trioxide and hydrogen peroxide were used (see Butler A. R.: J. Chem. Educ. 36, 508, 1971) and the aromatic iodination, catalyzed by metal halogenides, was reported as well (see Uemura S., Onoe A., Okano M, Bull. Chem. Soc. Jpn. 47, 147, 1974).

Recently Italian patent publication No. 19860 A/84, in the name of the Applicant, describes a process for the synthesis of aromatic iodo-substituted compounds starting from alkaline salts of aromatic acids, by reaction with iodine. In all the well known methods, the selectivities, with respect to iodine, are never higher than 90%; in a few methods use was made of expensive oxidative agents and in other methods one started from not easily available reactants.

Now we have found that the synthesis of iodobenzene can be carried out more conveniently according to the reaction:

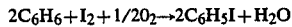

$$2C_6H_6 + I_2 + 1/2O_2 \rightarrow 2C_6H_5I + H_2O \qquad (I)$$

using $O_2$ as oxidative agent and a particular zeolite as catalyst.

DISCLOSURE OF THE INVENTION

In its most wide form, the invention relates to a method for the synthesis of iodobenzene in a gaseous phase, by iodination of benzene with iodine, in the presence of oxygen, air or another gas containing oxygen; in detail: a gaseous mixture containing benzene, iodine and the oxidative gas is conveyed onto a catalyst based on zeolites of ZSM 5 or ZSM 11 type, exchanged, before being used, with at least one bivalent or trivalent cation, preferably from the group comprising the $Mn^{++}$, $Co^{++}$, $Zn^{++}$, $Fe^{++}$ and $Ni^{++}$ cations, as well as the cations of the alkaline-earth metals.

The zeolitic catalysts may be used as such or mixed with a suited amount of an inert agent, for instance $SiO_2$, acting as a binder and/or a carrier.

When a zeolite, according to the invention, is used as catalyst, a stabilization of the catalytic activity is noted. When, on the contrary, the same zeolites are used in the acid or alkaline form, a decay of said activity is noted. Furthermore, in the case of zeolites having a low $SiO_2/Al_2O_3$ ($\leq 10$) ratio, the acid form can not be absolutely used, as a structure collapse takes place under the reaction conditions or during the possible reactivation.

For the catalysts preparation we can start both from the sodic and from the acid form. In the first case the sodium is exchanged with the desired cation, using known methods; when, on the contrary, one starts from zeolites in the acid form, although the exchange technique can be still used, it is more convenient to resort to the neutralization technique, using an aqueous solution of a salt of a cation giving by hydrolysis a basic pH or even better a diluted solution of the hydroxide of a metal cation. This latter method gives assurance of a zeolite free from Brönsted acid sites. The catalytic system can also consist of zeolites, having two or more metal cations.

The iodination can be carried out according to the most different techniques, without swerving from the spirit of the invention. By way of example, however, the following general directions are advisable for carrying out the process. An iodine solution in benzene (concentration from 0.5 to 50%, preferably from 5 to 20% by weight) is evaporated and mixed with air in such amount that the air/$I_2$ molar ratio is at least equal to the stoihiometric one and preferably $\geq 10$. The resultant mixture is conveyed to a fixed bed reactor, loaded with the catalyst, the temperature ranging between 200° and 550° C. (preferably between 350° and 450° C.) and the space velocity (WHSV) ranging between 0.1 and 100 (preferably between 1 and 20) Kg/h of benzene per Kg of the active part of the catalyst (binder excluded); use can also be made of an inert diluent, such as, for instance, nitrogen, helium or steam. The products can then be recovered by cooling the gaseous flow leaving the reactor and by resorting to usual treatments. In case of distillation, the overhead distilled benzene can be recycled to the iodination reactor. The global pressure used during the tests is almost always slightly higher than the atmospheric one; lower or higher pressures, however, may be used as well. The catalyst maintains its activity a long time, particularly when one works, in a gas phase, at 300°–450° C.; however, when the catalitic activity falls below the allowable levels, regeneration is required. An excellent regeneration consists in activating the catalyst in benzene-air mixtures for a few hours at temperatures between 300° and 600° C. The starting activation of the catalyst is an important element as well.

The following examples will illustrate the invention, without limiting however the scope thereof.

EXAMPLE 1

(Comparative; H-ZSM 5)

A ZSM 5 zeolite was prepared in a raw form, according to example 24 of U.S. Pat. No. 3,702,886 and was then exchanged at 80° C. with a 1M solution of HCl in order to obtain the H-ZSM 5 form free from sodium; the zeolite crystallites had an average size below 0.5 μm.

1 g of the thus obtained H-ZSM 5 zeolite was mixed with 0,3 g of binder ($SiO_2$) and the whole was activated in the air for 2 hours at 540° C. The resultant catalyst was loaded into a quartz microreactor, kept at 400° C. by means of a thermostat and continuosly fed with a gaseous mixture of benzene, iodine and air, having a benzene:iodine:air molar ration=20:1:20. The pressure was slightly higher than 760 mm/Hg and the space velocity (WHSV) was 6 Kg/h of benzene/iodine mixture per Kg of zeolite. The reaction was run for 1 hour and the reaction products were gathered by condensation. The iodine conversion was 65% and the molar selectivity to iodobenzene (with respect to benzene) 98.6%; after 6 hours the conversion lowered to about 25%.

EXAMPLE 2

(Comparative; Na-ZSM 5)

1 g of H-ZSM 5 zeolite, prepared as described in example 1 and bound with 0.3 g of $SiO_2$, was suspended in 20 cm³ of deionized water and neutralized with a 0.1M solution of NaOH; the suspension (at pH 8) was heated up to 80° C.; if pH was tending to lower, NaOH was added up to a persistent pH 8. The suspension was filtered and the solid was washed with deionized water, dried in an oven at 110° C. for 2 hours and activated at 540° C. for further 2 hours. The operative conditions of example 1 were then repeated, using the thus obtained Na-ZSM 5 zeolite; after 2 hours the iodine conversion was not higher than 20%.

EXAMPLE 3

(Ca-ZSM 5)

Example 2 was repeated, while replacing the NaOH solution with an equivalent $Ca(OH)_2$ solution, using for the iodination the thus obtained Ca-ZSM 5 zeolite; data and results are set forth in Table 1.

EXAMPLE 4

(Zn-ZSM 5)

1 g of H-ZSM 5 zeolite prepared as described in Example 1 and bound with 0.3 g of $SiO_2$, was exchanged three times at 80° C. with 20 cm³ (at a time) of a 0.5M solution of zinc acetate; when the exchange was over the zeolite was washed with deionized water, dried at 110° C. for 2 hours and activated at 540° C. for further 2 hours. Example 1 was then repeated by using the thus prepared Zn-ZSM 5 zeolite as catalysts; data and results are set forth on Table 1.

EXAMPLE 5

(Co-ZSM 5)

Example 4 was repeated, while using a saturated solution of $Co^{++}$ acetate instead of zinc acetate; data and results are set forth on Table 1.

EXAMPLE 6

Example 5 was repeated, lowering the reaction temperature to 350° C.; data and results are on Table 1.

EXAMPLE 7

Example 4 was repeated, while using a solution of $Mn^{++}$ acetate, instead of zinc acetate; data and results are set forth on Table 1.

EXAMPLES 8–13

Examples 3–7 were repeated, while warying slightly the operative parameters (flow and/or temperature); data and results are set forth in Table 1.

EXAMPLE 14

(Ba-ZSM 5)

Example 4 was repeated, while replacing the solution of zinc acetate with a solution of barium hydroxide; data and results are set forth on Table 1.

EXAMPLE 15

(Comparative; K-ZSM 5)

Example 14 was repeated replacing $Ba(OH)_2$ with potassium hydroxide; data and results are set forth on Table 3.

EXAMPLE 16

(Al-ZSM 5)

Example 14 was repeated replacing $Ba(OH)_2$ with aluminum hydroxide; data and results are set forth in Table 3.

EXAMPLE 17

(Mg-ZSM 5)

Example 14 was repeated, while replacing $Ba(OH)_2$ with magnesium acetate, thereby obtaining similar results.

EXAMPLE 18

(Mg-ZSM 11)

Example 17 was repeated replacing the ZSM 5 zeolite with a Zsm 11 zeolite, thereby obtaining substantially similar results.

EXAMPLE 19

(Mg-Mn-ZSM 5)

Example 7 was repeated, while using a 50/50 mixture (by moles) of $Mn^{++}$ acetate and Mg acetate; the results were slightly better both compared with Example 7 and with Example 17.

TABLE 1

| Ex. | Zeolite | T (°C.) | WHSV (h⁻¹) | Conv. $I_2$ (%) 1 h | Conv. $I_2$ (%) 6 h | Selectivity (%) $C_6H_5I$ 1 h | $C_6H_5I$ 6 h | $C_6H_4I_2$ 1 h | $C_6H_4I_2$ 6 h | others 1 h | others 6 h |
|---|---|---|---|---|---|---|---|---|---|---|---|
| 1* | H—ZAM5 | 400 | 6 | 65 | 25 | 98.6 | n.d. | — | — | — | — |
| 2* | Na—ZSM5 | 400 | 6 | — | 20(2 h) | — | — | — | — | — | — |
| 3 | Ca—ZSM5 | 400 | 6 | — | 99.5 | — | 97.5 | — | 2.2 | — | 0.3 |
| 4 | Zn—ZSM5 | 400 | 6 | — | 90.0 | — | 98.6 | — | 1.2 | — | 0.2 |
| 5 | Co—ZSM5 | 400 | 6 | — | 99 | — | 98.5 | — | 1.3 | — | 0.2 |
| 6 | Co—ZSM5 | 350 | 6 | — | 98.6 | — | 98.5 | — | 1.4 | — | 0.1 |
| 7 | Mn—ZSM5 | 400 | 6 | — | 99.6 | — | 97.8 | — | 2.1 | — | 0.1 |
| 8 | Ca—ZSM5 | 400 | 5.7 | 100 | 99.0 | 97.0 | 98.0 | 2.8 | 1.8 | 0.2 | 0.2 |
| 9 | Ca—ZSM5 | 350 | 5.7 | 99 | 78 | 98.0 | 98.5 | 1.9 | 1.5 | 0.1 | — |
| 10 | Mn—ZSM5 | 400 | 5.7 | 99.0 | 99.4 | 97.4 | 97.6 | 2.2 | 2.3 | 0.5 | 0.2 |
| 11 | Mn—ZSM5 | 350 | 5.7 | 96.3 | 80.0 | 98.3 | 98.8 | 1.5 | 1.0 | 0.2 | 0.2 |
| 12 | Zn—ZSM5 | 400 | 5.7 | 81.0 | 91.7 | 96.3 | 98.3 | 1.4 | 1.1 | 2.3 | 0.6 |
| 13 | Co—ZSM5 | 400 | 5.7 | 99.7 | 99.0 | 98.6 | 98.4 | 1.3 | 1.6 | 0.1 | — |
| 14 | Ba—ZSM5 | 400 | 5.7 | 82 | 75 | 98.6 | 98.5 | 1.4 | 1.5 | — | — |
| 15* | K—ZSM5 | 400 | 5.7 | 5 | — | 98 | — | 2.0 | — | — | — |

TABLE 1-continued

| Ex. | Zeolite | T (°C.) | WHSV (h$^{-1}$) | Conv. I$_2$ (%) | | Selectivity (%) | | | | | |
|---|---|---|---|---|---|---|---|---|---|---|---|
| | | | | | | C$_6$H$_5$I | | C$_6$H$_4$I$_2$ | | others | |
| | | | | 1 h | 6 h | 1 h | 6 h | 1 h | 6 h | 1 h | 6 h |
| 16 | Al—ZSM5 | 400 | 5.7 | 87 | 50 | 98.4 | 97.9 | 1.4 | 1.9 | 0.2 | 0.2 |

*Comparative.

We claim:

1. In a method for the synthesis of iodobenzene by the catalytic oxidative iodination of benzene, at 200° to 550° C. and in the gaseous phase, with iodine and elemental oxygen or an oxygen-containing gas, the improvement consisting essentially in that the catalyst is selected from the class consisting of zeolites of the ZSM5 type and zeolites of the ZSM11 type, exchanged with a bivalent or trivalent metal cation.

2. A method according to claim 1, wherein oxidizing agent is air and wherein the air/I$_2$ molar ratio is equal to or higher than the stoichiometrical ratio and preferably $\geq 10$.

3. A method according to claim 1, wherein the concentration of iodine in the feed benzene ranges from 0.5 to 50%.

4. A method according to claim 1, wherein the space velocity ranges between 0.1 and 100 Kg/h of benzene per Kg of pure zeolite, binder excluded.

5. A method according to claim 1, wherein the zeolite is exchanged, before being used, with at least a cation selected from the group consisting of Zn$^{++}$, Co$^{++}$, Mn$^{++}$ and the alkaline-earth cations.

6. A method according to claim 1, wherein the oxyiodination temperature ranges from 350° to 450° C.

7. A method for the synthesis of iodobenzene, wherein benzene, iodine and air or another gas containing oxygen, are brought into contact with a zeolite of ZSM 5 type, exchanged with at least a cation selected from the group consisting of Zn$^{++}$, Mn$^{++}$ and Ca$^{++}$, at temperatures ranging between 350° and 450° C. and according to air/I$_2$ molar ratios equal to or higher than 8, the space velocity ranging between 1 and 100 Kg/h of benzene per Kg of pure zeolite and iodine being fed as a benzenic solution at 5–20% by weight.

* * * * *